Jan. 16, 1973 C. H. SAURET Plant Pat. 3,294
ALMOND TREE
Filed June 7, 1971
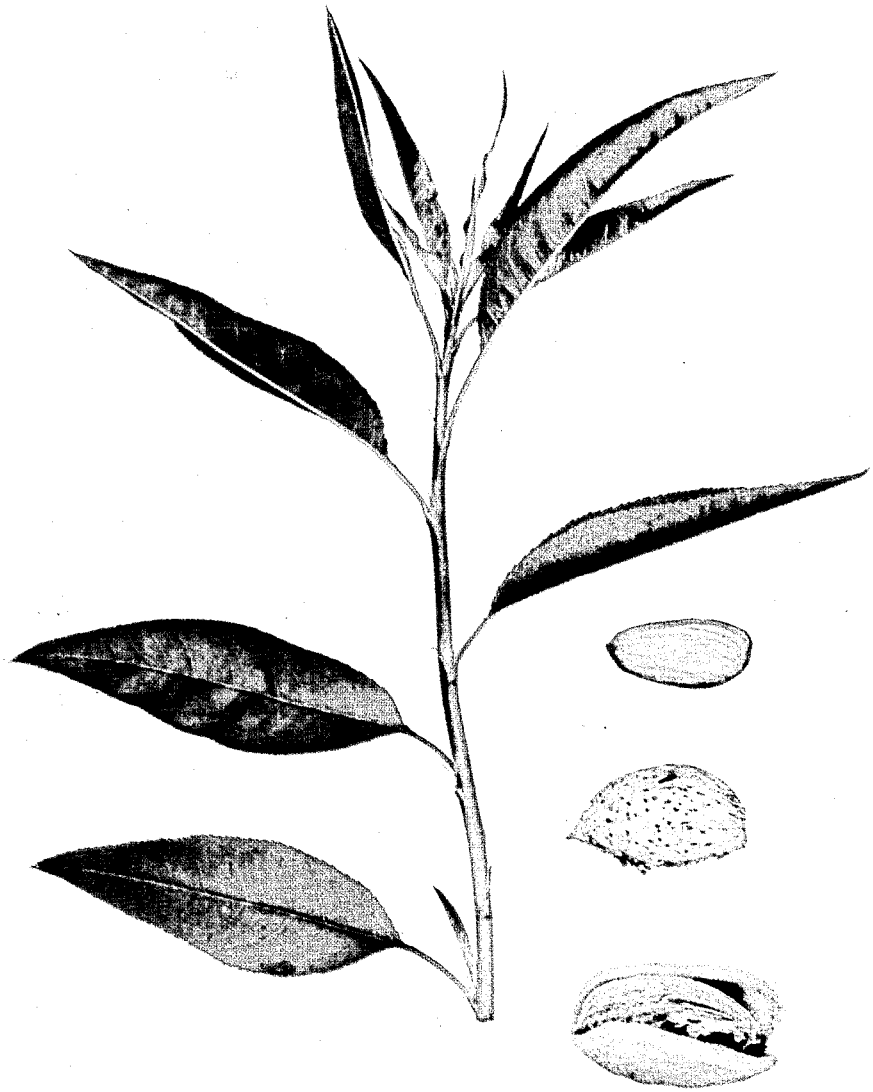
INVENTOR
Clarence H. Sauret
BY
Webster & Webster
ATTORNEYS United States Patent Office Plant Pat. 3,294
Patented Jan. 16, 1973

3,294
ALMOND TREE

Clarence H. Sauret, Paso Robles, Calif., assignor of a fractional part interest to Richard K. Sauret, Paso Robles, Calif.

Filed June 7, 1971, Ser. No. 150,854
Int. Cl. A01h 5/03
U.S. Cl. Plt.—30 1 Claim

ABSTRACT OF THE DISCLOSURE

An almond tree characterized by large size, vigorous and dense growth, abundant foliage with medium-size ovate leaves, and regular and heavily clustered production of large, well-distributed nuts which hang well on the tree and are easy to harvest and process; the variety blooming closely with and pollinating the Nonpareil (unpatented) and harvesting about ten days before the Mission (unpatented); the nuts, of good quality and good flavor, averaging 300 per pound; the percentage of kernel to nut averaging 60%; and the kernels averaging 29.3 per ounce.

ORIGIN OF THE VARIETY

The present variety of almond tree was discovered by me growing as a chance seedling in an orchard—of which at the time of such discovery I was an owner—located in the Oak Flat area of San Luis Obispo County, Calif. When such seedling (which I maintained under close and continuing observation) matured and bore a crop, I recognized that it had certain new and distinctive characteristics which made the variety desirable for commercial growing.

ASEXUAL REPRODUCTION OF THE VARIETY

After my discovery of the variety as a chance seedling, and recognition by me of its desirable characteristics, I asexually reproduced the variety by grafting on mature Davey (unpatented) trees in the aforementioned orchard. In maturity, such reproductions ran true to the parent tree in all respects.

SUMMARY OF THE VARIETY

The herein claimed variety provides a commercially desirable almond tree which blooms closely with and pollinates the Nonpareil, while being particularly characterized, as to novelty, by the regular and heavily clustered production of large, well-distributed nuts which hang well on the tree, and are easy to harvest and process; the variety harvesting about ten days before the Mission; the nuts, of good quality and good flavor, averging 300 per pound; the percentage of kernel to nut averaging 60%; and the kernels averaging 29.3 per ounce.

The herein claimed variety of almond tree is further characterized by a tree of large size, vigorous and dense growth, and abundant foliage with medium-size ovate leaves.

BRIEF DESCRIPTION OF THE DRAWING

The drawing is an illustration, by photographic reproduction in color, of a twig with leaves, a nut in hull, a nut out of hull, and a separate kernel.

DESCRIPTION OF THE VARIETY

The botanical details of this new and distinct variety of almond tree—with color definitions in common color terms—are as follows:

Tree:
- *Size.*—Large.
- *Density.*—Dense.
- *Vigor.*—Vigorous.

Trunk: Form—average.

Branches:
- *Form.*—Medium.
- *Texture.*—Tough.
- *Branching habit.*—Upright to spreading.
- *Lenticels.*—Average number; average size.

Foliage: Quantity—abundant.

Leaves:
- *Size.*—Medium; average length—79 mm.; average width—25 mm.
- *Shape.*—Ovate.
- *Thickness.*—Medium to thin.
- *Texture.*—Smooth.
- *Margin.*—Crenate.
- *Petiole.*—Medium.
- *Glands.*—Average number—1 to 4; opposite; medium size.
- *Color.*—Dark green.

Bloom:
- *Amount of bloom.*—Heavy.
- *Color.*—Pinkish.
- *Blooming period.*—About 3 days after Nonpareil; spans 20 to 25 days.

Crop:
- *Bearing.*—Regular bearer.
- *Productivity.*—Heavily clustered.
- *Distribution of nuts on tree.*—Well distributed.
- *Harvest period.*—10 days before Mission.
- *Tenacity.*—Hangs well on tree; easy to harvest; easy to process.

Hull:
- *Outer surface.*—Rough; irregular.
- *Form.*—Irregular.
- *Thickness.*—Medium.
- *Flesh.*—Tough.
- *Suture.*—Ridged.
- *Color at harvest.*—Yellow to brown.
- *Dehiscence.*—Wide.
- *Splitting.*—Along suture.

Nut:
- *Size.*—Large; average length—38 mm.; average width—23 mm.; average thickness—20 mm.; nuts (in shell) per pound on average sample—300.
- *Form.*—Length/width—elongated. Width/thickness—large to rounded.
- *Shell.*—Medium thin. Outer shell—Crumbly. Inner shell—ragged; medium hard; well sealed.
- Color.—Tan.
- *Pits.*—Large; irregular; deep.
- *Base.*—Ventrally oblique.
- *Stem scar.*—Large.
- *Apex.*—Acute; sharp.
- *Wing.*—Medium; narrow; thin.
- *Inner surface.*—Tan.
- *Ventral streak.*—Light; narrow; long.
- *Percentage of kernel to nut on average sample.*—60%.

Kernel:
- *Size.*—Large; average length—26 mm.; average width—13 mm.; average thickness—10 mm.
- *Kernels per ounce on average sample.*—29.3.
- *Form.*—Length/width—elongated. Width/thickness—equal.
- *Stem scar.*—Variable.
- *Apex.*—Acute; sharp,
- *Surface.*—Smooth.
- *Pellicle.*—Thin.
- *Pubescence.*—None.
- *Color.*—Brown.
- *Number of doubles.*—Very few—no more than 1%.
- *Defective kernels.*—Very rarely.
- *Deformed kernels.*—Very rarely.

*Flavor.*—Good.

*Quality.*—Good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is characterized by large size, vigorous and dense growth, abundant foliage with medium-size ovate leaves, and regular and heavily clustered production of large, well-distributed nuts which hang well on the tree and are easy to harvest and process; the variety blooming closely with and pollinating the Nonpareil and harvesting about ten days before the Mission; the nuts, of good quality and good flavor, being relatively high in average percentage of kernel to nut.

No references cited.

ROBERT E. BAGWILL, Primary Examiner